United States Patent
Prabhakar et al.

(10) Patent No.: US 9,442,273 B2
(45) Date of Patent: Sep. 13, 2016

(54) OPTIMIZED IMAGING APPARATUS FOR IRIS IMAGING

(71) Applicant: DELTA ID INC., Fremont, CA (US)

(72) Inventors: Salil Prabhakar, Fremont, CA (US); Valentine Dvorovkin, Santa Cruz, CA (US)

(73) Assignee: Delta ID Inc., Fremont, CA (US)

( * ) Notice: Subject to any disclaimer, the term of this patent is extended or adjusted under 35 U.S.C. 154(b) by 0 days.

(21) Appl. No.: 14/899,885

(22) PCT Filed: Jun. 18, 2014

(86) PCT No.: PCT/US2014/042834
§ 371 (c)(1),
(2) Date: Dec. 18, 2015

(87) PCT Pub. No.: WO2014/205020
PCT Pub. Date: Dec. 24, 2014

(65) Prior Publication Data
US 2016/0148048 A1    May 26, 2016

Related U.S. Application Data

(60) Provisional application No. 61/836,444, filed on Jun. 18, 2013.

(51) Int. Cl.
*H04N 5/232* (2006.01)
*H04N 5/225* (2006.01)
*G06K 9/00* (2006.01)
*G02B 13/00* (2006.01)
*A61B 3/12* (2006.01)
(Continued)

(52) U.S. Cl.
CPC ......... *G02B 13/0015* (2013.01); *A61B 3/1216* (2013.01); *G02B 5/208* (2013.01); *G06K 9/00604* (2013.01); *G06K 9/00617* (2013.01); *H04N 5/2254* (2013.01); *H04N 5/23212* (2013.01); *H04N 5/23245* (2013.01); *A61B 5/117* (2013.01)

(58) Field of Classification Search
CPC .......... H04N 5/23212; H04N 5/2254; H04N 5/23245; G06K 9/00604
See application file for complete search history.

(56) References Cited

U.S. PATENT DOCUMENTS 4,871,238 A * 10/1989 Sato ................. G02B 15/10
359/675
6,289,113 B1   9/2001 McHugh et al.
7,277,561 B2  10/2007 Shin
(Continued)

*Primary Examiner* — Abdelaaziz Tissire
(74) *Attorney, Agent, or Firm* — Hoffmann & Baron, LLP

(57) ABSTRACT

The invention comprises a method for configuring an imaging apparatus having an image sensor and an optical assembly. The method modifies a first imaging configuration of the imaging apparatus to achieve a second imaging configuration of said imaging apparatus, by interposing a refractive optical element between an image-side surface of the optical assembly and an imaging surface. In another embodiment, the method modifies a first imaging configuration of the imaging apparatus to achieve a second imaging configuration of said imaging apparatus by removing the refractive optical element from between an image-side surface of the optical assembly and an imaging surface. The invention additionally includes an imaging apparatus configured for switching from a first imaging configuration to a second imaging configuration. At least one of the first imaging configuration and the second imaging configuration may be configured for iris imaging.

25 Claims, 6 Drawing Sheets

(51) Int. Cl.
*G02B 5/20* (2006.01)
*A61B 5/117* (2016.01)

(56) References Cited

U.S. PATENT DOCUMENTS

| | | | |
|---|---|---|---|
| 7,761,453 B2 | 7/2010 | Hamza | |
| 8,064,647 B2 | 11/2011 | Bazakos et al. | |
| 8,090,246 B2 * | 1/2012 | Jelinek | G06K 9/00604 |
| | | | 348/296 |
| 9,366,843 B2 * | 6/2016 | Prabhakar | G06K 9/00604 |
| 2002/0024732 A1 * | 2/2002 | Hamano | G02B 15/173 |
| | | | 359/557 |
| 2004/0239785 A1 * | 12/2004 | Nanjo | G02B 7/102 |
| | | | 348/294 |
| 2005/0243411 A1 * | 11/2005 | Cook | G02B 13/146 |
| | | | 359/363 |
| 2008/0316619 A1 * | 12/2008 | Yu | G02B 13/001 |
| | | | 359/811 |
| 2010/0110275 A1 * | 5/2010 | Mathieu | A61B 3/14 |
| | | | 348/360 |
| 2012/0102332 A1 * | 4/2012 | Mullin | G06F 1/1626 |
| | | | 713/186 |
| 2013/0113921 A1 * | 5/2013 | Richards | G02B 27/46 |
| | | | 348/135 |
| 2015/0071503 A1 * | 3/2015 | Prabhakar | G06K 9/00617 |
| | | | 382/117 |

* cited by examiner

OPTIMIZED IMAGING APPARATUS FOR IRIS IMAGING

CROSS-REFERENCE TO RELATED APPLICATIONS

This application is a National Stage Application under 35 U.S.C. §371 of PCT Application No. PCT/US2014/042834, filed on Jun. 18, 2014, which claims priority to U.S. Provisional Patent Application No. 61/836,444, filed on Jun. 18, 2013, the entire contents of which are incorporated by reference herein

FIELD OF INVENTION

The invention relates to an imaging apparatus and method, which imaging apparatus and method enables obtaining images of one or more features of a subject's eye for biometric identification. The invention is particularly operable for optimizing imaging apparatuses for iris image capture and iris recognition.

BACKGROUND

Methods for biometric identification based on facial features, including features of the eye are known. Methods for iris recognition implement pattern-recognition techniques to compare an acquired image of a subject's iris against a previously acquired image of the subject's iris, and thereby determine or verify identity of the subject. A digital template corresponding to an acquired iris image is encoded based on the image, using mathematical/statistical algorithms. The digital template is compared against databases of previously encoded digital templates (corresponding to previously acquired iris images), for locating a match and thereby determining or verifying identity of the subject.

Apparatuses for iris recognition may comprise an imaging apparatus for capturing an image of the subject's iris(es) and an image processing apparatus for comparing the captured image against previously stored iris image information. The imaging apparatus and image processing apparatus may comprise separate devices, or may be combined within a single device.

While iris recognition apparatuses have been previously available as dedicated or stand alone devices, it is increasingly desirable to incorporate iris recognition capabilities into mobile communication devices or mobile computing devices (collectively referred to as "mobile devices") having inbuilt cameras, such as for example, mobile phones, smart phones, personal digital assistants, tablets or laptop devices.

It has however been found that cameras within mobile devices are intended to operate as general purpose cameras, capable of capturing images of objects situated at a wide range of distances from the mobile device. The considerations for acquiring iris images for the purpose of biometric recognition are significantly different from considerations applicable to image capture of non-iris images. Specifically, iris imaging particularly necessitates positioning of a subject's iris within a defined image capture region, such that the iris image acquired by the imaging apparatus satisfies a minimum pixel resolution in the object plane. Given the size of the iris, and pixel size of image sensors typically used in mobile device cameras, configuring a camera to capture an iris image having suitable iris diameter in the image plane, requires a specific object distance (i.e. distance at which the subject's iris requires to be positioned). Configuring a camera inbuilt into a mobile device in this manner may render the camera unsuitable for multiple uses (such as for iris imaging while retaining general purpose photography capabilities) by requiring that the object be placed very close to the camera to obtain images having appropriate sharpness and detail.

Prior art solutions for altering an object plane of a camera typically involve a zoom lens type arrangement, where the lens assembly comprises a number of individual lenses that may slide axially along the body of the lens assembly to change focal length and magnification of the lens assembly. However, zoom lenses are expensive and bulky, both of which provide serious disincentives for use in cameras inbuilt into mobile devices.

Another concern that arises from dual use of fixed focus cameras, is that iris image capture typically relies on infrared (IR) wavelengths, whereas non-iris image capture usually seeks to eliminate IR wavelengths by using IR cut filters (filters which reflect or absorb IR wavelengths, while allowing visible wavelengths to pass through the lens assembly and on to the image sensor).

It is therefore an objective of the invention to provide efficient and cost effective mechanisms to configure an iris imaging apparatus or camera built into a mobile device such that the iris imaging apparatus or camera can be optimized for iris imaging.

SUMMARY

The invention comprises a method for configuring an imaging apparatus having an image sensor and an optical assembly, the optical assembly comprising an image-side surface and an object-side surface and configured for imaging an object plane onto an imaging surface of the image sensor. The method modifies a first imaging configuration of the imaging apparatus to achieve a second imaging configuration of said imaging apparatus, wherein modifying the first imaging configuration comprises interposing a refractive optical element between the image-side surface of the optical assembly and the imaging surface.

The method may alternatively comprise modifying a first imaging configuration of the imaging apparatus to achieve a second imaging configuration of said imaging apparatus, wherein modifying the first imaging configuration comprises removing the refractive optical element from between the image-side surface of the optical assembly and the imaging surface.

In another embodiment, the invention comprises an imaging apparatus configured for switching from a first imaging configuration to a second imaging configuration. The apparatus comprises an image sensor having an imaging surface, an optical assembly including an image-side surface and an object-side surface, and a refractive optical element. In the first imaging configuration, the optical assembly images onto the imaging surface, an in-focus image of an object positioned at a first object plane located a first object distance away from object-side surface of the optical assembly. In the second imaging configuration, the optical assembly images onto the imaging surface, an in-focus image of an object positioned at a second object plane located a second object distance away from the object-side surface of the optical assembly. The refractive optical element within the apparatus may be configured to be interpositioned between the image-side surface of the optical assembly and the image sensor to switch from the first imaging configuration to the second imaging configuration.

The refractive optical element in either method or apparatus embodiments may be configured to (i) shift an image-side principal plane of the optical assembly, by a shift distance in the direction of the imaging surface, and (ii) shift an image-side focal plane of the optical assembly, by the shift distance in the direction of the imaging surface. In the first imaging configuration, the optical assembly may image onto the imaging surface, an in-focus image of an object positioned at a first object plane located a first object distance away from the object-side surface of the optical assembly. In the second imaging configuration the optical assembly may image onto the imaging surface, an in-focus image of an object positioned at a second object plane located a second object distance away from the object-side surface of the optical assembly, such that the second object distance is greater than the first object distance. For the purposes of the invention, the shift distance is a distance between a first image plane at which the optical assembly images an in-focus image of an object positioned at the first object plane, and a second image plane at which the optical assembly images an in-focus image of an object positioned at the second object plane.

In an embodiment of the invention, width and refractive index of the refractive optical element may be selected such that the image-side principal plane and image-side focal plane of the optical assembly shift in the direction of the imaging surface, by the shift distance.

One of the first and second imaging configurations of the invention may be optimized for iris imaging. In an embodiment, the first imaging configuration is optimized for iris imaging.

The refractive optical element may in an embodiment be a plano-parallel element. The plano-parallel element may include an optical filter. In an embodiment where the first imaging configuration is optimized for iris imaging, the optical filter may be an infra-red pass filter. When the second imaging configuration is optimized for iris imaging, the optical filter may be an infra-red cut filter.

The optical assembly of the imaging apparatus may be a fixed focus optical assembly. In an embodiment of the invention, at least one, or both of focal length of the optical assembly, and distance between the imaging surface and the image-side surface of the optical assembly, may remain constant in both the first and second imaging configurations.

There may be other optical elements between positioned the interposed element and the imaging surface. These other optical elements may include, but are not limited to parts of the image sensor, such as a plano-parallel cover glass, a color mask, other optical filters, a micro-lens, conventional lens elements etc.

BRIEF DESCRIPTION OF THE ACCOMPANYING DRAWINGS

DETAILED DESCRIPTION

Figure 1:
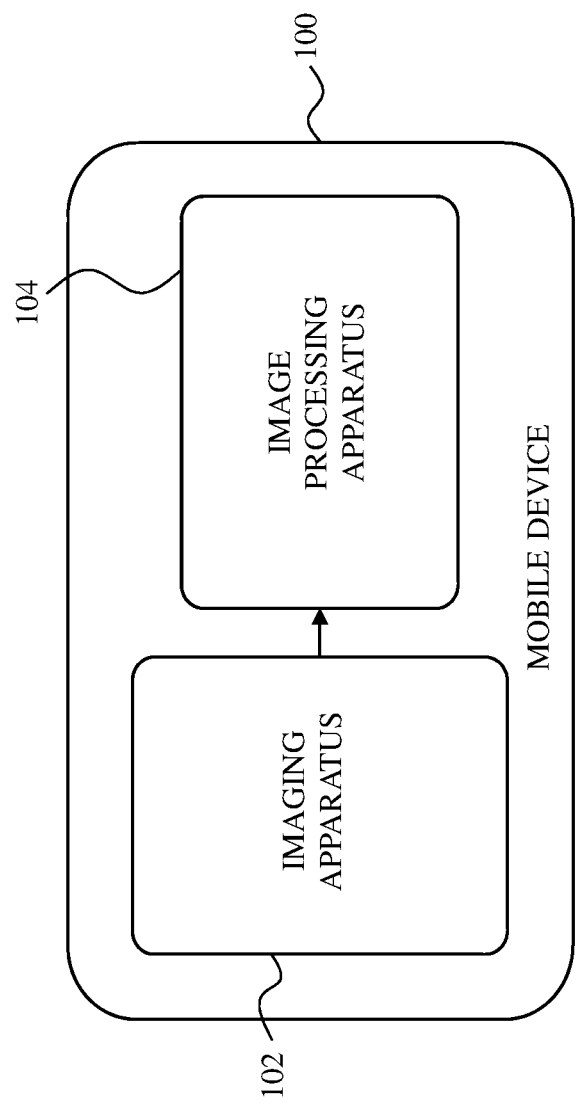
FIG. 1 is a functional block diagram of a mobile device configured for iris image based recognition.

FIG. 1 is a functional block diagram of a mobile device 100 configured for iris image based recognition, comprising an imaging apparatus 102 and an image processing apparatus 104. Imaging apparatus 102 acquires an image of the subject's iris and transmits the image to image processing apparatus 104. The image captured by imaging apparatus 102 may be a still image or a video image. Image processing apparatus 104 thereafter analyses the acquired image frame (s) and compares the corresponding digital feature set with digital templates encoded and stored based on previously acquired iris images, to identify the subject, or to verify the identity of the subject.

Although not illustrated in FIG. 1, mobile device 100 may include other components, including for extracting still frames from video images, for processing and digitizing image data, for enrolment of iris images (the process of capturing, and storing iris information for a subject, and associating the stored information with that subject) and comparison (the process of comparing iris information acquired from a subject against information previously acquired during enrolment, for identification or verification of the subject's identity), and for enabling communication between components of the mobile device. The imaging apparatus, image processing apparatus and other components of the mobile device may each comprise separate devices, or may be combined within a single mobile device.

Figure 2:
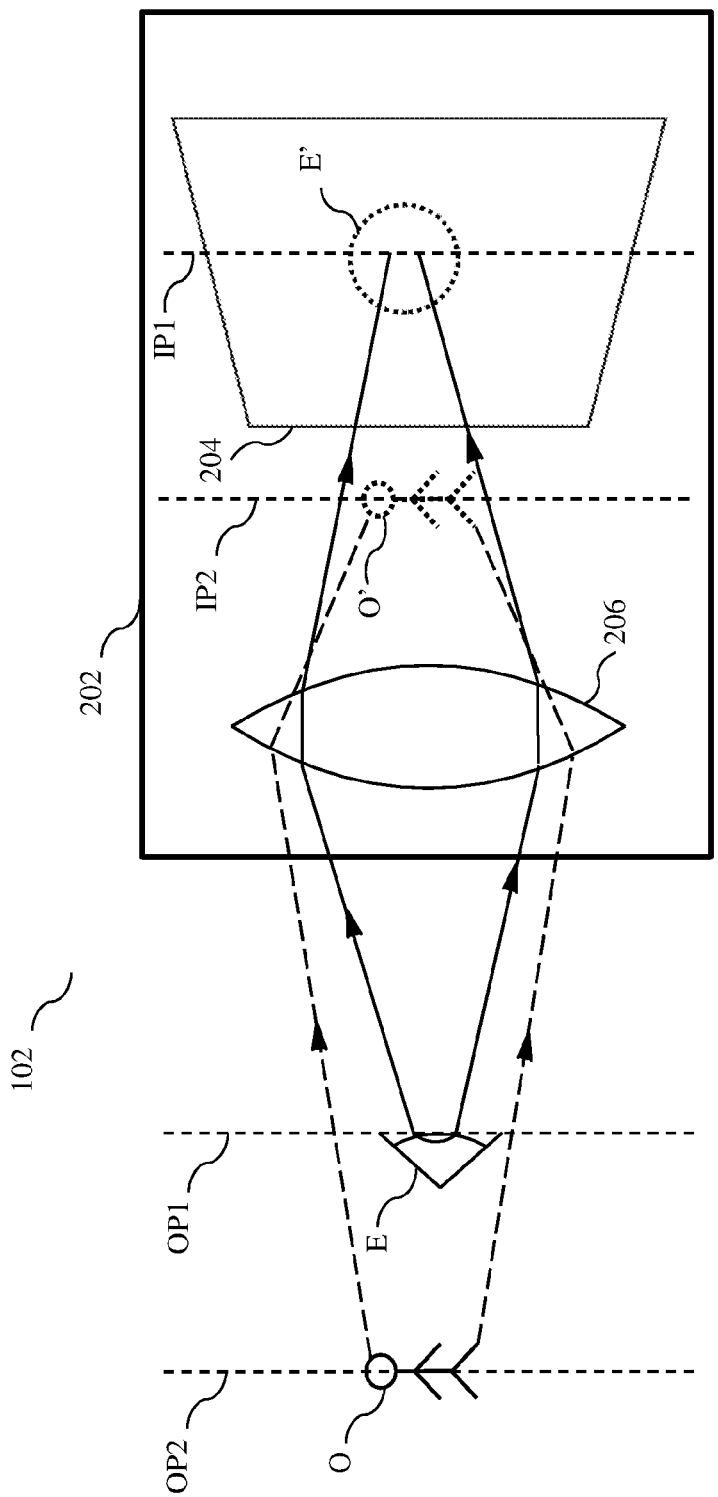
FIG. 2 illustrates an embodiment of an imaging apparatus.

FIG. 2 illustrates an exemplary embodiment of imaging apparatus 102 having housing 202, image sensor 204 and an optical assembly 206, wherein image sensor 204 and optical assembly 206 are disposed within the housing 206.

Imaging apparatus 102 may comprise a conventional solid state still camera or video camera, and image sensor 204 may comprise a charged coupled device (CCD) or a complementary metal oxide semiconductor (CMOS) device. Image sensor 204 may be selected for sensitivity at least to light having wavelengths anywhere in the range of 400 nanometers nm to 1000 nanometers. Optical assembly 206 may comprise an integrally formed or single unitarily formed element, or may comprise an assembly of optical elements selected and configured for achieving desired image forming properties. The imaging apparatus as illustrated has a fixed focus, of a type that is conventionally disposed within mobile devices.

The illustration in FIG. 2 exemplifies a problem faced in adapting fixed focus cameras that is intended for general purpose photography, to a configuration which enables iris imaging, or vice versa. As shown in FIG. 2, optical assembly 206 and image sensor 204 may be configured and disposed relative to each other, such that when a subject's eye E is positioned at object plane OP1, an in-focus image E' of the eye is formed at image plane IP1, which image plane coincides with an imaging surface of image sensor 204. On the other hand, given the fixed focus configuration of the illustrated imaging apparatus, when an object O is positioned at object plane OP2 (which object plane OP2 is located further away from the imaging apparatus in comparison to object plane OP1), an image O' of the object is formed at image plane IP2, which image plane does not coincide with the imaging surface of image sensor 204—and thereby causes an out-of-focus image to acquired by image sensor 204. The shift in object plane accordingly causes a shift in image plane, which shift cannot be compensated for in a fixed focus optical assembly.

Based on the above, it is apparent that configuring a camera to capture an iris image having suitable iris diameter in the image plane requires a specific object distance (i.e. distance at which the subject's iris requires to be positioned). Configuring a camera inbuilt into a mobile device in this manner, may render the camera unsuitable for other uses as a result of a configuration that requires an object to be placed very close to the camera for obtaining images having appropriate sharpness and detail.

The present invention provides an apparatus and methods for optimizing imaging apparatuses for iris imaging and also for general purpose photography, without requiring changes to focal length of the optical assembly.

To ensure that a fixed focus imaging apparatus configured for general photography (such as of a kind provided within a mobile device) is enabled to capture iris images of sufficient resolution for iris image recognition processing, a subject's iris is required to be positioned at an object plane that is closer to the optical assembly of the imaging apparatus than is ordinarily considered acceptable for general purpose photography. As discussed above in connection with FIG. 2, for a fixed focus camera, changing the position of an object plane has a corresponding effect on position of the resulting image plane, such that the image plane may no longer coincide with the imaging surface of an image sensor—and resulting in out-of-focus image acquisition. This causes problems when trying to configure a camera to switch between a general purpose photography mode, and an iris image acquisition mode, since intended object planes for the two modes are located at significantly different distances from the optical assembly of the imaging apparatus. For example, it has been found that for fixed focus imaging apparatuses disposed within mobile devices, configuring the imaging apparatus for iris imaging requires the iris to be moved to within 250 mm from an object-side surface of an optical assembly. In contrast, requiring objects to be positioned within 250 mm of an object-side surface of an optical assembly would be highly impractical for general purpose photography.

Figure 3:
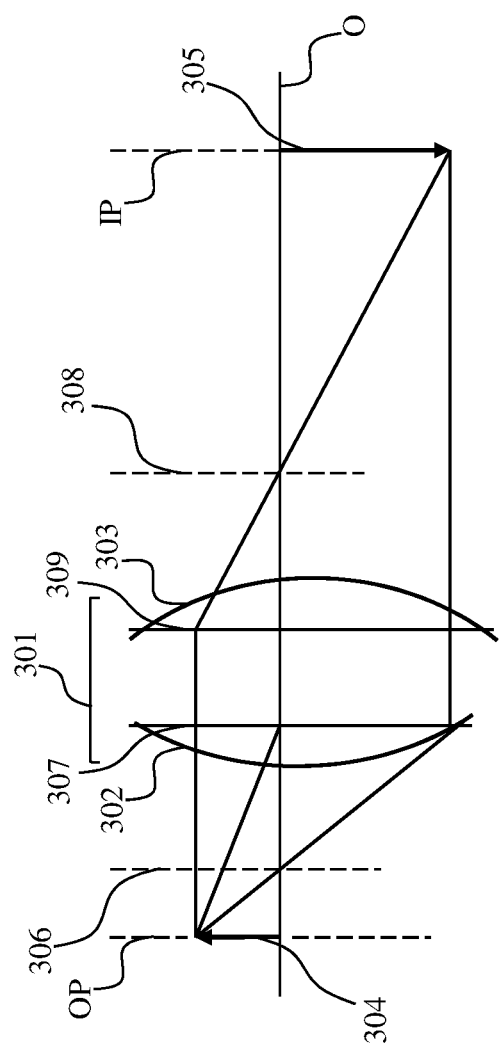
FIG. 3 illustrates cardinal planes of an imaging apparatus.

For the purposes of explaining configurations for an imaging apparatus in accordance with the present invention, FIG. 3 illustrates various cardinal planes of an iris imaging apparatus. The illustration of FIG. 3 comprises an optical assembly 301 interpositioned between object plane OP and image plane IP, such that for an object 304 positioned at object plane OP, an in-focus image 305 is formed at image plane IP.

Optical assembly 301 may be configured and positioned such that image plane IP coincides with an imaging surface of an image sensor within the imaging apparatus. In the illustrated embodiment, optical assembly 301 comprises an object-side surface 302, and an image-side surface 303. Cardinal planes of optical assembly 301 include an object-side focal plane 306, an object-side principal plane 307, and an image-side focal plane 308 and an image-side principal plane 309.

For the purposes of this invention, in accordance with paraxial approximation, it is understood that the term "focal plane" refers to a plane where incident rays parallel to an optical axis of a lens assembly would converge at a point. The term "principal plane" refers to a plane where each incident ray parallel to an optical axis of a lens assembly intersects with a corresponding ray exiting the lens assembly.

For a lens assembly having focal length F, object distance S (distance between the object-side focal plane of the lens assembly and the object plane) and image distance S' (distance between the image-side focal plane of the lens assembly and the image plane/image sensor):

$$\frac{1}{F} = \frac{1}{S} + \frac{1}{S'}$$

Accordingly, for an imaging apparatus having a lens assembly with a fixed focal length, reducing an object distance S to achieve iris image capture of sufficient detail for iris image processing would require a corresponding increase in the image distance S' to ensure that the image formed on the image sensor remains sharp and in-focus.

In view that the optical lens assembly within a mobile device imaging apparatus is ordinarily not moveable relative to the image sensor, the invention provides a mechanism for responding to changes in object distance by changing the image distance without varying either of (i) the focal length of the lens assembly and (ii) the physical distance between the rear most surface of the lens assembly and the image sensor.

In an embodiment of the invention, the invention responds to a change in object distance by selectively interposing or removing a refractive optical element between the rear focal plane of the lens assembly and the image sensor. The refractive optical element is selected and positioned such that for a given object distance $S_0$, at which an in-focus image of the object would ordinarily be formed at image distance $S'_0$, the refractive optical element rearwardly shifts the image-side principal plane and the image-side focal plane of the lens assembly towards the image sensor, thereby increasing effective image distance to $S'_1$. As explained in greater detail below, by increasing the effective image distance, the invention compensates for reduction in object distance (without requiring a corresponding shift of the image sensor away from the fixed focus lens assembly) by increasing the effective image distance such that an in-focus image of the object continues to be formed on the image sensor.

Figure 4:
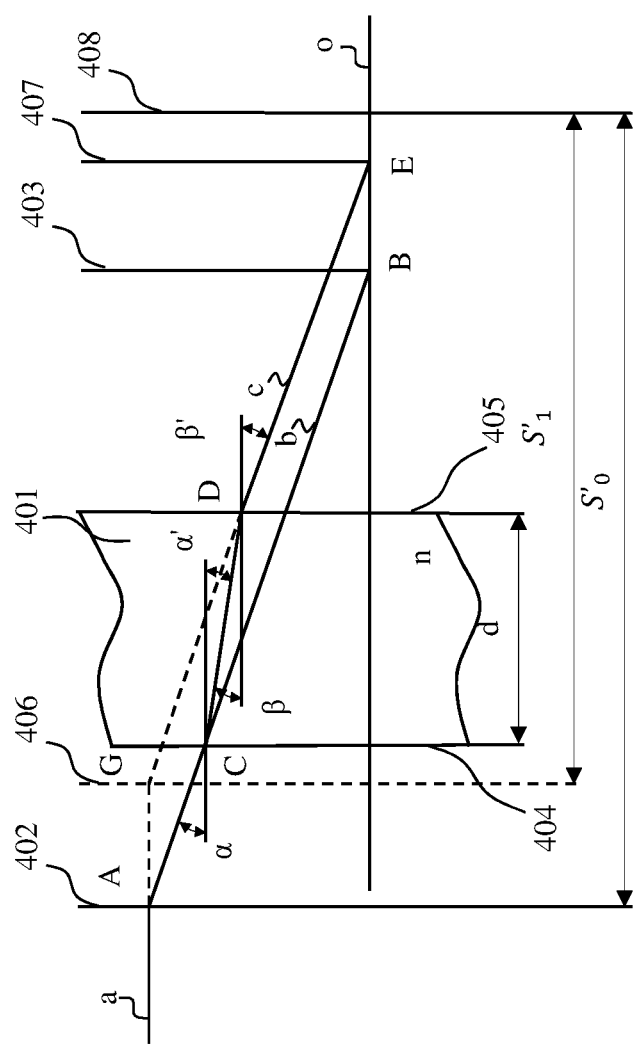
FIGS. 4, 5 and 6 illustrate effects of adding a refractive optical element between an optical lens assembly and an image sensor within an imaging apparatus.

FIG. 4 illustrates the principles discussed in the immediately preceding paragraphs.

FIG. 4 illustrates the effects of adding a refractive optical element (such as a plano-parallel optical element) between the lens assembly and the image sensor. The refractive optical element in FIG. 4 is a plano-parallel refractive element 401. The actual components of the imaging apparatus and the ray trace through the optical lens assembly are not shown in FIG. 4.

In FIG. 4, taking first the situation where plano-parallel refractive element 401 is not interpositioned between the optical lens assembly and an image plane 408, ray a parallel to optical axis o enters the lens assembly and exits the lens assembly as ray b. The point of intersection of ray a and ray b is point A that defines image-side principal plane 402. The effective path of output ray b is AB, such that point B lies at the intersection between exit ray b and optical axis o and defines image-side focal plane 403.

When plano-parallel element 401 is interposed in the system, ray a parallel to optical axis o enters the lens assembly, exits the lens assembly, follows path AC, refracts at point C on an object side surface 404 of plano-parallel element 401, follows path CD within plano-parallel element 401, and then refracts at D on an image-side surface 405 of plano-parallel element 401 and exits as ray c following path DE.

The intersection of DE and incident ray a defines new image-side principal plane 406, and the intersection of DE with optical axis o defines new image-side focal plane 407 of the optical system that includes the plano-parallel element 401.

As illustrated in FIG. 4, exiting ray c is parallel to ray b because the angles α' and β are equal and correspondingly, angles α and β' are also equal. Focal length f of the optical system is:

$$f = S_{402\text{-}403} = S_{406\text{-}407}$$

As would be understood from the illustration of FIG. 4, focal length of the optical system remains the same with or without the plano-parallel element. However interposing the plano-parallel element effects a rearward shift (in the direction of the image plane/image sensor) in the image-side principal plane (from 402 to 406) and the image-side focal plane (from 403 to 407 of the optical system. The rearward shift of said two rear cardinal planes is to the extent of a fixed offset, which offset is a function of the thickness and the refractive index of the plano-parallel element.

Applying paraxial approximation to the system of FIG. 4, where:

$$\tan(\alpha) = \sin(\alpha) = \alpha, \quad (1)$$

$$\alpha' = \alpha/n \quad (2)$$

where α is the angle between the ray exiting the lens assembly 402 and the optical axis o, α' is the angle between the ray exiting the interposed plano-parallel optical element 401 and the optical axis o and n is the refractive index of the interposed plano-parallel optical element material 401.

The shift distance of the two rear cardinal planes $S_{402\text{-}406}$ and $S_{403\text{-}407}$ may be arrived at by:

$$S_{402-406} = S_{403-407} = \frac{(d \cdot \alpha - d \cdot \alpha')}{\alpha} = d \cdot \left(1 - \frac{1}{n}\right)$$

where d is thickness of the interposed plano-parallel optical element 401.

As is apparent from FIG. 4, the object-side principal plane and object-side focal plane of the system remain unchanged regardless of whether the plano-parallel element is interposed within the system.

Figure 5:
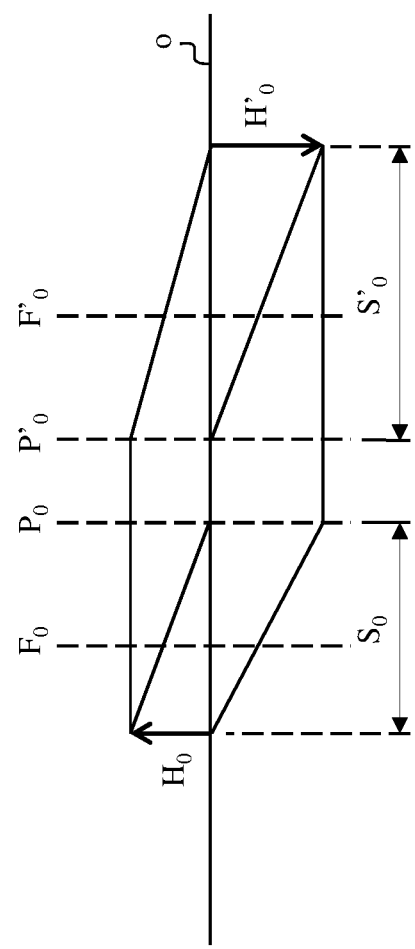
Figure 6:
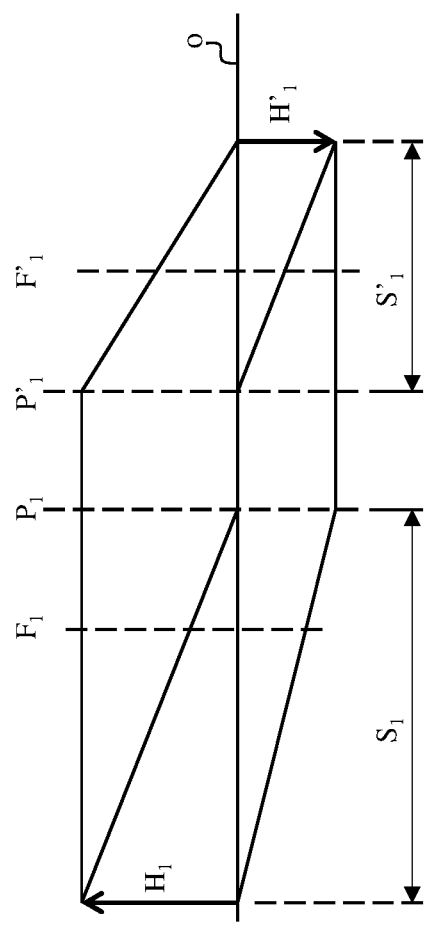

FIGS. 5 and 6 illustrate the manner in which interpositioning of a refractive optical element (such as a plano-parallel element) between an image-side focal plane of an optical assembly and the image sensor can be used to compensate for changes in object positions/object planes while achieving a desired magnification of the object.

FIG. 5 illustrates the effects of an optical system without a plano-parallel refractive element, while FIG. 6 illustrates the effects of an optical system having the plano-parallel element interposed therein It will be understood that FIG. 6 does not specifically depict the actual plano-parallel element within the optical system.

In FIG. 5 (illustrating an optical system without the plano-parallel element):
$F_0$=object-side focal plane
$F'_0$=image-side focal plane
$P_0$=object-side principal plane
$P'_0$=image-side principal plane
$H_0$=height of the object
$H'_0$=height of the image
$S_0$=object distance (distance between object-side principal plane $P_0$ and the object) and
$S'_0$=image distance (distance between image-side principal plane $P'_0$ and the image formed on the image sensor).

Similarly, in FIG. 6 (illustrating optical system having the plano-parallel element disposed therein):
$F_1$=object-side focal plane
$F'_1$=image-side focal plane
$P_1$=object-side principal plane
$P'_1$=image-side principal plane
$H_1$=height of the object
$H'_1$=height of the image
$S_1$=object distance (distance between object-side principal plane $P_0$ and the object) and
$S'_1$=image distance (distance between image-side principal plane $P'_0$ and the image formed on the image sensor).

Based on a comparison of FIGS. 5 and 6, and the above disclosure in connection with FIG. 3, $S'_0 = S'_1 +$Shift Distance (i.e. $S_{402\text{-}406}$ from FIG. 4)

Applying the lens formula, $$\frac{1}{S_0} = \frac{1}{f} - \frac{1}{S'_0} = \frac{1}{f} - \frac{1}{S'_1 + \text{Shift Distance}} > \frac{1}{f} - \frac{1}{S'_1} = \frac{1}{S_1}$$

i.e $S_0 < S_1$

Based on FIGS. 4 to 6 and the above description, it can be understood that omitting or removing the refractive optical element (such as the plano-parallel element) from the imaging apparatus reduces the image distance while the focal length of the lens assembly and the image plane (position of the image sensor relative to the lens assembly) remains unchanged.

As explained in connection with FIG. 6, interposing the refractive optical element (such as the plano-parallel element) within the imaging apparatus allows for image capture at increased object distances (with a correspondingly larger linear field of view) without altering focal length of the lens assembly and the image plane (position of the image sensor).

In an embodiment, the imaging apparatus may be configured for iris image capture at reduced object distances necessary for iris imaging by removing the refractive optical element/plano-parallel element from the imaging apparatus. The imaging apparatus may be configured for non-iris image capture at increased object distances by interposing the refractive optical element in front of the image sensor, thereby achieving a desired rearward distance shift in the rear principal plane and rear focal plane of the optical system and reducing the effective image distance, without changing the position of the lens assembly and the image sensor.

In embodiments of the invention illustrated in FIGS. 5 and 6, the desired change in object distance and magnification is achieved by selectively adding or removing the plano-parallel element. In another embodiment, the desired change in object distance and magnification may be achieved by replacing a first refractive optical element/plano-parallel element with a different refractive optical element/plano-parallel element having either a different thickness or a different refractive index or both.

It would be understood that there may be other optical elements between positioned an interposed refractive element/plano-parallel and the imaging surface. These other optical elements may include, but are not limited to parts of the image sensor, such as a plano-parallel cover glass, a color mask, other optical filters, a micro-lens, conventional lens elements etc.

Interpositioning of the refractive element/plano-parallel element between an image-side surface of an optical assembly and an imaging surface may be achieved by manually inserting or removing said refractive element/plano-parallel element. In another embodiment, the invention may include one or more holders configured to accommodate the refractive element/plano-parallel element and having at least first and a second position. In the first position, the refractive element/plano-parallel element may be interposed between the imaging surface and the optical lens assembly, so as to image onto the imaging surface, objects positioned at a first object plane. In the second position, the refractive element/plano-parallel element may be removed from between the imaging surface and the optical lens assembly, so as to image onto the imaging surface, objects positioned at a second object plane. The one or more holders may alternatively be configured to hold at least two refractive elements/plano-parallel elements having differences in thickness, refractive index or both, and may be configured to interchangeably position one of the at least two refractive elements/plano-parallel elements between the imaging surface and the optical lens assembly. The refractive elements/plano-parallel elements may be configured and positioned such that interpositioning of the first refractive element/plano-parallel element between the imaging surface and the optical lens assembly causes in-focus imaging of a first object plane onto the imaging surface, and interpositioning of the second refractive element/plano-parallel element between the imaging surface and the optical lens assembly causes in-focus imaging of a second object plane onto the imaging surface.

Holders for removable positioning of plano-parallel elements may have any mechanical or eletromechanical configuration which enables positioning and removal of a refractive element/plano-parallel element between the image sensor and optical lens assembly. Exemplary configurations include rotating holders, pivoting arms, sliding window arrangements, and any other arrangement capable of adding or removing a refractive element/plano-parallel element in front of an image sensor, or replacing one refractive element/plano-parallel element with another refractive element/plano-parallel element in front of the image sensor.

By appropriately configuring the removable refractive element/plano-parallel element, the optical assembly can be configured to have a first set of image capture properties corresponding to interpositioning of the refractive element/plano-parallel element in front of the image sensor, and a second set of image capture properties corresponding to removal of the refractive element/plano-parallel element from in front of the image sensor.

In addition to modifying the image-side focal plane and image-side principal plane, a refractive element/plano-parallel element may also be selected to serve as an optical filter, including as an infra-red cut filter (for non-iris imaging modes) or as an infra-red pass filter (for iris imaging modes).

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

The invention claimed is:

1. A method for configuring an imaging apparatus comprising an image sensor and an optical assembly including an image-side surface and an object-side surface and configured for imaging an object plane onto an imaging surface of the image sensor, the method comprising:
modifying a first imaging configuration of the imaging apparatus to achieve a second imaging configuration of said imaging apparatus, wherein modifying the first imaging configuration comprises interposing a refractive optical element between the image-side surface of the optical assembly and the imaging surface, wherein the interposed refractive optical element is configured to:
(i) shift an image-side principal plane of the optical assembly, by a shift distance in the direction of the imaging surface; and
(ii) shift an image-side focal plane of the optical assembly, by the shift distance in the direction of the imaging surface;
wherein in the first imaging configuration, the optical assembly images onto the imaging surface, an in-focus image of an object positioned at a first object plane located a first object distance away from the object-side surface of the optical assembly;
wherein in the second imaging configuration the optical assembly images onto the imaging surface, an in-focus image of an object positioned at a second object plane located a second object distance away from the object-side surface of the optical assembly, such that the second object distance is greater than the first object distance;
and wherein the shift distance is a distance between a first image plane at which the optical assembly images an in-focus image of an object positioned at the first object plane, and a second image plane at which the optical assembly images an in-focus image of an object positioned at the second object plane.

2. The method as claimed in claim 1, wherein width and refractive index of the refractive optical element are selected such that the image-side principal plane and image-side focal plane of the optical assembly shift in the direction of the imaging surface, by the shift distance.

3. The method as claimed in claim 1, wherein one of the first and second imaging configurations is optimized for iris imaging.

4. The method as claimed in claim 3, wherein the first imaging configuration is optimized for iris imaging.

5. The method as claimed in claim 1, wherein the optical assembly is a fixed focus optical assembly.

6. The method as claimed in claim 1, wherein at least one of:
focal length of the optical assembly, and
distance between the imaging surface and the image-side surface of the optical assembly, is constant in both of the first and second imaging configurations.

7. A method for configuring an imaging apparatus comprising an image sensor and an optical assembly including an image-side surface and an object-side surface and configured for imaging an object plane onto an imaging surface of the image sensor, the method comprising:
modifying a first imaging configuration of the imaging apparatus to achieve a second imaging configuration of said imaging apparatus, wherein modifying the first imaging configuration comprises removing a refractive optical element from between the image-side surface of the optical assembly and the imaging surface, wherein the removed refractive optical element is configured to:
(i) shift an image-side principal plane of the optical assembly, by a shift distance in the direction of the imaging surface; and
(ii) shift an image-side focal plane of the optical assembly, by the shift distance in the direction of the imaging surface;
wherein in the first imaging configuration, the optical assembly images onto the imaging surface, an in-focus image of an object positioned at a first object plane located a first object distance away from the object-side surface of the optical assembly;

wherein in the second imaging configuration the optical assembly images onto the imaging surface, an in-focus image of an object positioned at a second object plane located a second object distance away from the object-side surface of the optical assembly, such that the first object distance is greater than the second object distance;

and wherein the shift distance is a distance between a first image plane at which the optical assembly images an in-focus image of an object positioned at the first object plane, and a second image plane at which the optical assembly images an in-focus image of an object positioned at the second object plane.

8. The method as claimed in claim 7, wherein width and refractive index of the refractive optical element are selected such that the image-side principal plane and image-side focal plane of the optical assembly shift in the direction of the imaging surface by the shift distance.

9. The method as claimed in claim 7, wherein one of the first and second imaging configurations is optimized for iris imaging.

10. The method as claimed in claim 9, wherein the refractive optical element is a plano-parallel element.

11. The method as claimed in claim 9, wherein the refractive optical element is a plano-parallel optical filter.

12. The method as claimed in claim 11, wherein when the first imaging configuration is optimized for iris imaging, the optical filter is an infra-red pass filter.

13. The method as claimed in claim 11, wherein when the second imaging configuration is optimized for iris imaging, the optical filter is an infra-red cut filter.

14. The method as claimed in claim 7, wherein the optical assembly is a fixed focus optical assembly.

15. The method as claimed in claim 7, wherein at least one of:
focal length of the optical assembly, and
distance between the imaging surface and the image-side surface of the optical assembly, is constant in both of the first and second imaging configurations.

16. An imaging apparatus configured for switching from a first imaging configuration to a second imaging configuration, the apparatus comprising:
an image sensor comprising an imaging surface;
an optical assembly including an image-side surface and an object-side surface and configured for imaging an object plane onto an imaging surface of the image sensor such that:
in the first imaging configuration, the optical assembly images onto the imaging surface, an in-focus image of an object positioned at a first object plane located a first object distance away from object-side surface of the optical assembly;
in the second imaging configuration, the optical assembly images onto the imaging surface, an in-focus image of an object positioned at a second object plane located a second object distance away from the object-side surface of the optical assembly; and
the second object distance is greater than the first object distance;
a refractive optical element configured to be interpositioned between the image-side surface of the optical assembly and the image sensor to switch from the first imaging configuration to the second imaging configuration, such that the interpositioned refractive optical element:
(i) shifts an image-side principal plane of the optical assembly, by a predefined shift distance in the direction of the imaging surface; and
(ii) shifts an image-side focal plane of the optical assembly, by the shift distance in the direction of the imaging surface;
wherein the shift distance is a distance between a first image plane at which the optical assembly images an in-focus image of an object positioned at the first object plane, and a second image plane at which the optical assembly images an in-focus image of an object positioned at the second object plane.

17. The imaging apparatus as claimed in claim 16, wherein the refractive optical element is configured to be removed from between the image-side surface of the optical assembly and the imaging surface to achieve the first imaging configuration.

18. The imaging apparatus as claimed in claim 17, wherein width and refractive index of the refractive optical element are selected such that the image-side principal plane and image-side focal plane of the optical assembly shift in the direction of the imaging surface, by the shift distance.

19. The imaging apparatus as claimed in claim 17, wherein one of the first and second imaging configurations is optimized for iris imaging.

20. The imaging apparatus as claimed in claim 19, wherein the refractive optical element is a plano-parallel element.

21. The imaging apparatus as claimed in claim 19, wherein the refractive optical element is a plano-parallel optical filter.

22. The imaging apparatus as claimed in claim 21, wherein when the first imaging configuration is optimized for iris imaging, the optical filter is an infra-red pass filter.

23. The imaging apparatus as claimed in claim 21, wherein when the second imaging configuration is optimized for iris imaging, the optical filter is an infra-red cut filter.

24. The imaging apparatus as claimed in claim 16, wherein the optical assembly is a fixed focus optical assembly.

25. The imaging apparatus as claimed in claim 16, wherein at least one of:
focal length of the optical assembly, and
distance between the imaging surface and the image-side surface of the optical assembly is constant in both of the first and second imaging configurations.

* * * * *